(12) United States Patent
Matsuda et al.

(10) Patent No.: US 7,569,039 B2
(45) Date of Patent: Aug. 4, 2009

(54) DISPOSABLE PULL-ON GARMENT

(75) Inventors: Toshiyuki Matsuda, Akashi (JP); Kenji Fujimoto, Higashinada-ku (JP); Hiroshi Nakahata, Higashinada-ku (JP)

(73) Assignee: The Procter & Gamble Company, Cincinnati, OH (US)

( * ) Notice: Subject to any disclaimer, the term of this patent is extended or adjusted under 35 U.S.C. 154(b) by 681 days.

(21) Appl. No.: 10/985,402

(22) Filed: Nov. 10, 2004

(65) Prior Publication Data

US 2005/0107764 A1    May 19, 2005

Related U.S. Application Data

(60) Provisional application No. 60/523,262, filed on Nov. 19, 2003.

(51) Int. Cl.
*A61F 13/496* (2006.01)
*A61F 13/64* (2006.01)

(52) U.S. Cl. .................. 604/385.29; 604/385.3; 604/392; 604/396

(58) Field of Classification Search . 604/385.24–385.3, 604/395–96, 385 A, 385 R, 385.1–385.2; 128/156
See application file for complete search history.

(56) References Cited

U.S. PATENT DOCUMENTS

| 5,292,316 | A | * | 3/1994 | Suzuki | .................. | 604/385.26 |
| 5,449,353 | A | * | 9/1995 | Watanabe et al. | ...... | 604/385.27 |
| 6,264,639 | B1 | | 7/2001 | Sauer | | |
| 6,478,786 | B1 | | 11/2002 | Glaug et al. | | |
| 6,726,669 | B2 | * | 4/2004 | Shimada et al. | ........ | 604/385.29 |
| 2002/0128617 | A1 | | 9/2002 | Roe et al. | | |
| 2002/0138065 | A1 | * | 9/2002 | Yeater et al. | ................. | 604/395 |
| 2003/0139726 | A1 | | 7/2003 | Gibbs | | |

FOREIGN PATENT DOCUMENTS

| EP | 0761194 A2 | * | 3/1997 |
| EP | 1060721 A2 | * | 12/2000 |
| EP | 1 184 012 A1 | | 3/2002 |
| EP | 1219273 A2 | * | 7/2002 |
| EP | 1 269 955 A | | 1/2003 |
| JP | H-4-144558 | | 5/1992 |
| WO | WO94/09736 A1 | * | 5/1994 |
| WO | WO02/085273 A1 | * | 10/2002 |

* cited by examiner

*Primary Examiner*—Karin M Reichle
(74) *Attorney, Agent, or Firm*—Eric T. Addington; Amy M. Foust; Laura L. Whitmer

(57) ABSTRACT

A disposable pull-on garment includes an absorbent main body and a ring-like elastic belt forming a waist opening and two leg openings. The absorbent main body has longitudinal side edges and transverse end edges. The elastic belt includes a front belt and a back belt each having a transverse waist border and a transverse abdomen border. In the back belt, a waist border elastic material is disposed adjacent to the waist border between the waist border and the end edge of the absorbent main body, a side elastic material is disposed adjacent to the abdomen border, and a waist anchoring elastic material is disposed between them. A leg opening angle formed by the abdomen border and each of the longitudinal side edges of the absorbent main body is greater when the disposable pull-on garment is in a contracted configuration than when the disposable pull-on garment is in an uncontracted configuration.

9 Claims, 13 Drawing Sheets

DISPOSABLE PULL-ON GARMENT

CROSS REFERENCE TO RELATED APPLICATIONS

This Application claims the benefit of U.S. Provisional Application No. 60/523,262, filed Nov. 19, 2003.

FIELD OF THE INVENTION

The present invention relates to disposable pull-on garments which are donned by inserting the wearer's legs into the leg openings and sliding the garment up into position about the lower torso.

BACKGROUND OF THE INVENTION

Many pull-on diapers use elastic elements secured in an elastically contractible condition in the waist and leg openings. Typically, in order to insure full elastic fit about the leg and the waist such as is provided with durable undergarments, the leg openings and waist opening are encircled with elasticized bands of rubber or other materials positioned along the curve of the opening. Examples of such pull-on diapers are disclosed in EP 1 184 012 A1 published on Mar. 6, 2002. The pull-on diaper disclosed therein comprises an absorbent body and an exterior member covering the absorbent body and forming a contour of the diaper. The absorbent body is substantially rectangular and comprises a liquid-permeable topsheet, a liquid-impermeable backsheet and an absorbent core interposed therebetween. The leg and waist elastic members are provided at the body-surrounding portion in the exterior member to form an elasticized leg opening and an elasticized waist opening. The longitudinal sides of the exterior member are trimmed to form leg openings. While trimming the longitudinal sides of the exterior member allows the desired shape of curved leg opening to be formed, it requires an additional process for trimming and wastes raw materials.

Another example of pull-on diapers is disclosed in Japanese Laid-open Publication No. H4-144558 published on May 19, 1992. The pull-on diaper disclosed therein comprises an absorbent main body and an elastic belt joined to the front region and the back region of the absorbent main body. The upper end of the elastic belt defines a waist opening. The lower end of the elastic belt and the longitudinal side of the absorbent main body jointly define a leg opening. The elastic belt extends in the transverse direction of the diaper and the absorbent main body extends in the longitudinal direction. Therefore, the lower end of the elastic belt and the longitudinal side of the absorbent main body intersect at a right angle to define the leg opening. Such a configuration having an angular shape gives a poor aesthetic appearance impression to the user when the user takes a fresh diaper out of the bag, as compared with a pull-on diaper having a desired shape of curved leg opening.

Based on the foregoing, there is a need for a disposable pull-on garment having an aesthetic appearance while providing a cost advantage in forming a pull-on diaper. None of the existing disposable pull-on garment provides all of the advantages and benefits of the present invention.

SUMMARY OF THE INVENTION

The present invention is directed to a disposable pull-on garment having a waist opening and leg openings and extending in a longitudinal direction and a transverse direction. The pull-on garment comprises an absorbent main body and a ring-like elastic belt. The absorbent main body comprises a liquid pervious topsheet, a liquid impervious backsheet and an absorbent core disposed therebetween. The absorbent main body has longitudinal side edges, transverse end edges, a front waist panel, a back waist panel and a crotch panel. The front waist panel and the back waist panel are not joined directly. The ring-like elastic belt is surrounded by a transverse waist border and a transverse abdomen border. The ring-like elastic belt has a central panel and side panels. The central panel is joined to the front waist panel and the back waist panel of the absorbent main body to form one waist opening and two leg openings. The ring-like elastic belt is not disposed in the crotch panel of the absorbent main body. The ring-like elastic belt comprises a belt layer and a belt elastic material joined to the belt layer. The belt elastic material is provided with the belt layer such that the leg opening angle formed by the transverse abdomen border of the side panel and the longitudinal side edge of the absorbent main body is greater when the disposable pull-on garment is in a contracted configuration than when the disposable pull-on garment is in an uncontracted configuration.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

DETAILED DESCRIPTION OF THE INVENTION

As used herein, the term "pull-on garment" refers to articles of wear which have a defined waist opening and a pair of leg openings and which are pulled onto the body of the wearer by inserting the legs into the leg openings and pulling the article up over the waist. The term "disposable" is used herein to describe garments which are not intended to be laundered or otherwise restored or reused as a garment (i.e., they are intended to be discarded after a single use and, preferably, to be recycled, composted or otherwise disposed of in an environmentally compatible manner). The pull-on garment is also preferably "absorbent" to absorb and contain the various exudates discharged from the body. A preferred embodiment of the pull-on garment of the present invention is the disposable absorbent pull-on garment, pull-on diaper 20, shown in FIG. 1. As used herein, the term "pull-on diaper" refers to pull-on garments generally worn by infants and other incontinent individuals to absorb and contain urine and feces. It should be understood, however, that the present invention is also applicable to other pull-on garments such as training pants, incontinent briefs, feminine hygiene garments or panties, and the like.

Figure 1:
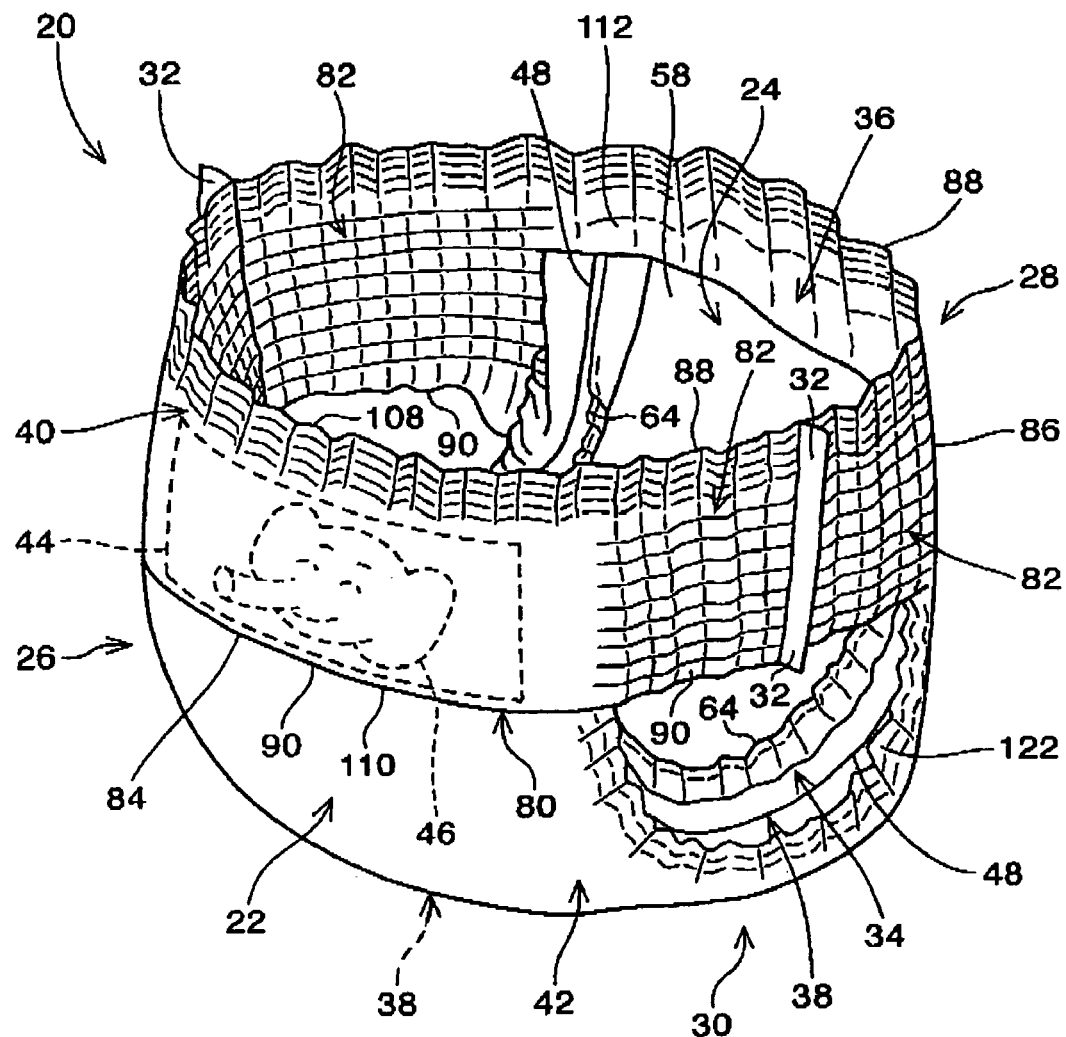
FIG. 1 is a perspective view of the disposable pull-on garment of the present invention in a typical in-use configuration.

FIG. 1 is a perspective view of the pull-on diaper 20 of the present invention. The pull-on diaper 20 has an outer surface 22, an inner surface 24 opposed to the outer surface 22, a front region 26, a back region 28, a crotch region 30, and seams 32 which join the front region 26 and the back region 28 to form leg openings 34 and a waist opening 36. The diaper 20 comprises an absorbent main body 38 (hereinafter may be referred to as "main body") to cover the crotch region of the wearer, a ring-like elastic belt 40 (hereinafter may be referred to as "elastic belt" or "belt") extending transversely about the waist opening 36, and an outer cover layer 42 to cover the main body 38. The elastic belt 40 defines the waist opening 36, and the elastic belt 40 and the main body 38 jointly defines the leg opening 34. The pull-on diaper 20 also has a patch sheet 44 printed with a graphic 46 thereon which may be disposed in the front region 26 and/or the back region 28.

The absorbent main body 38 absorbs and contains body exudates disposed on the main body 38. In the embodiment shown in FIG. 2, the main body 38 has a generally rectangular shape having a longitudinal centerline L, longitudinal side edges 48 and transverse end edges 50. The main body 38 also has a front waist panel 52 positioned in the front waist region 26 of the diaper 20, a back waist panel 54 positioned in the back waist region 28, and a crotch panel 56 in the crotch region 30.

Figure 3:
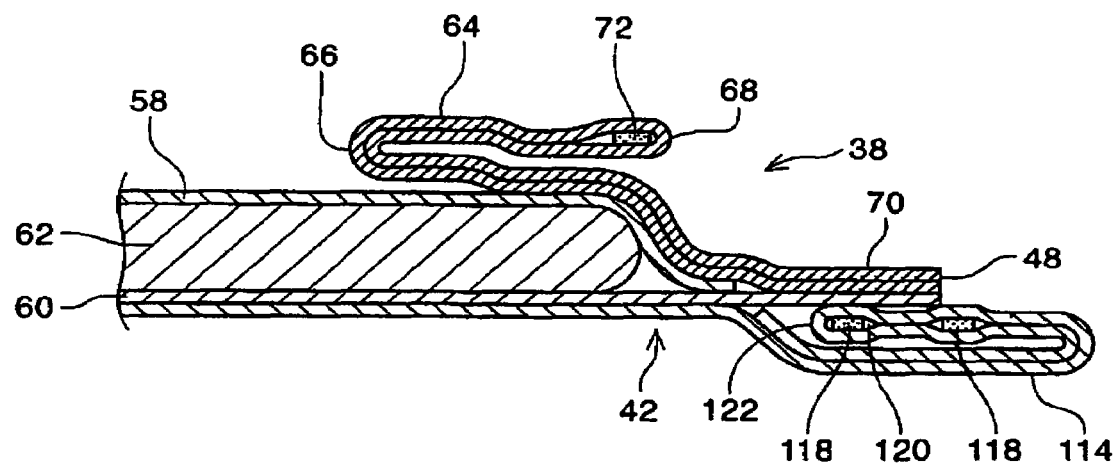
FIG. 3 is a cross-sectional view of FIG. 2 taken along the line III-III.
Figure 4:
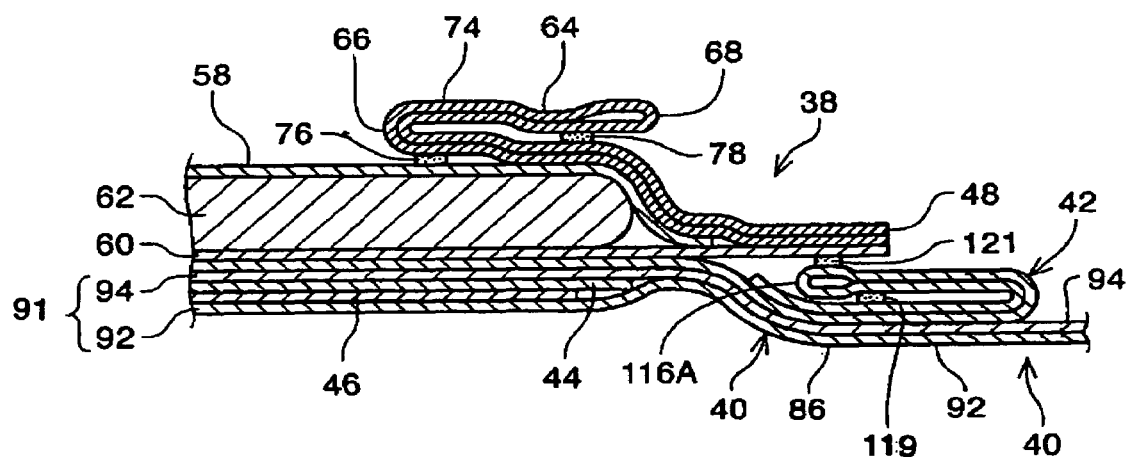
FIG. 4 is a cross-sectional view of FIG. 2 taken along the line IV-IV.

The main body 38 comprises a liquid pervious topsheet 58, a liquid impervious backsheet 60 and an absorbent core 62 disposed therebetween. The main body 38 may additionally comprise a barrier leg cuff 64 disposed along the longitudinal side edge 48. The barrier leg cuff 64 provides improved containment of liquids and other body exudates in the crotch region 30. The barrier leg cuff 64 shown in FIG. 3 comprises a single layer of material which is folded into two layers. The barrier leg cuff 64 extends from the longitudinal side edge 48 toward the longitudinal centerline L and then is folded along the folding line 66 back toward the longitudinal side edge 48. The barrier leg cuff 64 has a barrier cuff elastic material 72 at the distal edge 68. The proximal edge 70 of the barrier leg cuff 64 is joined to the backsheet 60 adjacent the longitudinal side edge 48. The portion of the barrier leg cuff 64 along the folding line 66 and the distal edge 68 are free from attachment to any portion of the main body 38 in the crotch panel 56 such that the barrier leg cuff 64 stands up toward the wearer's body when the diaper 20 is used. The transverse end 74 of the barrier leg cuff 64 is joined to the topsheet 58 adjacent the folding line 66 by an attachment means 76 which may be any known means such as an adhesive and is joined to the barrier leg cuff 64 itself along the distal edge 68 by an attachment means 78 which may be any known means such as an adhesive as shown in FIG. 4.

The liquid pervious topsheet 58 is preferably positioned adjacent the body-facing surface of the absorbent core 62 and may be joined thereto and/or to the backsheet 60 by any attachment means known in the art. The liquid impervious backsheet 60 is generally that portion of the diaper 20 positioned adjacent the garment-facing surface of the absorbent core 62 and prevents the exudates absorbed and contained therein from soiling articles that may contact the diaper 20. The absorbent core is positioned between the topsheet 58 and the backsheet 60 and absorbs and retains liquids such as urine and other certain body exudates. The topsheet 58, the backsheet 60 and the absorbent core may be manufactured any known materials. Suitable topsheet materials may include porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Suitable backsheet materials may include breathable materials that permit vapors to escape from the diaper while still preventing exudates from passing through the backsheet. Suitable absorbent core materials may include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The ring-like elastic belt 40 extends transversely about the waist opening 36 of the diaper 20 and acts to dynamically create fitment forces and to distribute the forces dynamically generated during wear. The elastic belt 40 comprises a front belt 84 and a back belt 86 (hereinafter may be collectively referred to as "front and back belt 84, 86") which are joined at the seam 32 to form a pull-on diaper having a waist opening and two leg openings. Each of the front belt 84 and the back belt 86 has a central panel 80 and side panels 82 positioned transversely outward from the central panel 80. Each of the front belt 84 and the back belt 86 also has a transverse waist border 88 and a transverse abdomen border 90. The transverse waist border 88 defines the waist opening 36. The central panel 80 of the front belt 84 may partly or entirely overlap with the front waist panel 52 of the main body 38. The central panel 80 of the back belt 86 may partly or entirely overlap with the back waist panel 54 of the main body 38. However, the central panel 80 of the front and back belt 84, 86 does not extend into the crotch panel 56 of the main body 38 and is not disposed in the crotch panel 56. In the embodiment shown in FIG. 2, the central panel 80 of the front belt 84 and the back belt 86 partly overlaps with the front waist panel 52 and the back waist panel 54, respectively.

Figure 2:
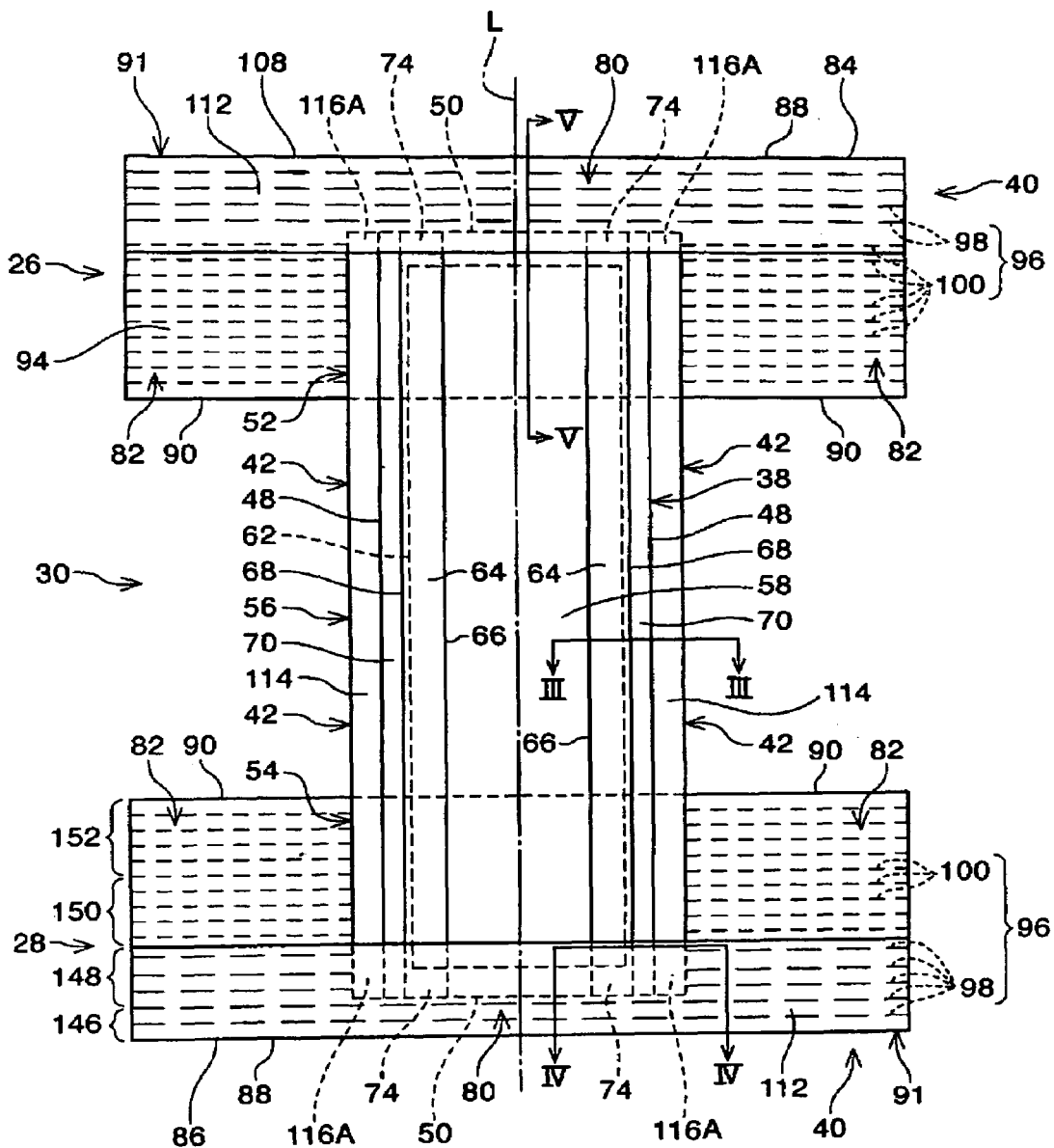
FIG. 2 is a top plan view of the pull-on garment in its flat uncontracted condition showing the inner surface.
Figure 5:
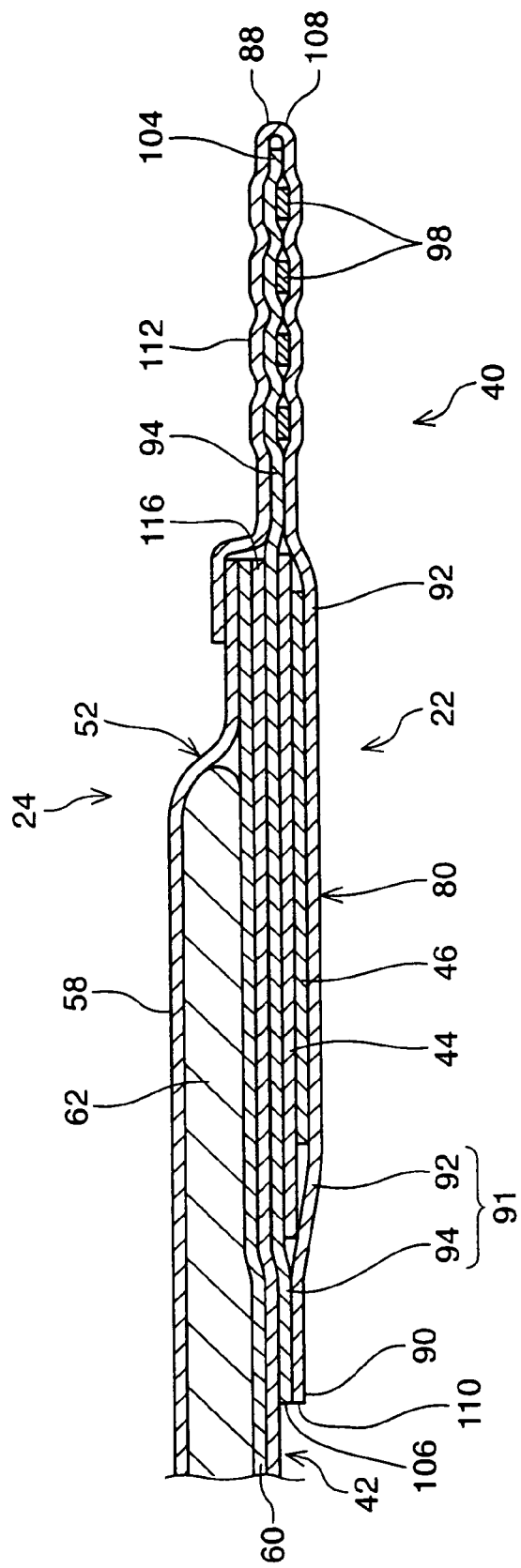
FIG. 5 is a cross-sectional view of FIG. 2 taken along the line V-V.

The ring-like elastic belt 40 comprises a belt layer 91 including an outer layer 92. The belt layer 91 further comprises an inner layer 94. A belt elastic material 96 is interposed between the outer layer 92 and the inner layer 94. The front belt 84 and the back belt 86 may comprise the same materials and/or may have the same structure. Alternatively, the front belt 84 and the back belt 86 may comprise different materials and/or may have different structures. As shown in the embodiment of FIG. 2, the front belt 84 and the back belt 86 generally have the same structure. Referring to FIG. 5, the inner layer 94 has a transverse waist edge 104 and a transverse abdomen edge 106. The outer layer 92 has a transverse waist end 108 and a transverse abdomen end 110. The inner layer 94 is almost coextensive with the contour of the front and back belt 84, 86. Alternatively, the inner layer 94 may be smaller than the size of the front and back belt 84, 86. The outer layer 92 of the belt layer 91 is longer than the size of the inner layer 94 in the longitudinal direction and an end flap 112 of the outer layer 92 is folded to cover the transverse waist edge 104 of the inner layer 94 at the waist opening 36 and to form a transverse waist end 108 of the outer layer 92. The inner layer 94 of the belt layer 91 may also have an end flap which may be folded together with the end flap 112 of the outer layer 92. The end flap of the inner layer 94 may be longer or shorter than or equal to the end flap of the outer layer 92. Alternatively, the end flap 112 may be eliminated such that the outer layer 92 terminates at the waist opening 36 to form a transverse waist end 108. In the embodiment shown in FIGS. 2 and 5, the transverse waist end 108 and the transverse abdomen end 110 of the outer layer 92 correspond to the transverse waist border 88 and the transverse abdomen border 90 of the front and back belt 84, 86, respectively. The outer layer 92 surrounded by the transverse waist end 108 and the transverse abdomen end 110 defines the shape of the front and back belt 84, 86 in the embodiment shown in FIGS. 2 and 5.

The front and back belt 84, 86 may have any shape to provide a ring-like belt. In the embodiment shown in FIG. 2, the transverse abdomen border 90 and the transverse waist border 88 extends transversely straight and in parallel to each other. Alternatively, the transverse abdomen border 90 may be shaped such that the longitudinal length between the transverse waist border 88 and the transverse abdomen border 90 in the central panel 80 is longer or shorter than the longitudinal length between the transverse waist border 88 and the transverse abdomen border 90 in the side panel 82.

The front and back belt 84, 86 may comprise any known materials. Suitable material for the front and back belt 84, 86 can be manufactured from a wide range of materials such as plastic films; apertured plastic films; woven or nonwoven webs of natural materials (e.g., wood or cotton fibers), synthetic fibers (e.g., polyolefins, polyamides, polyester, polyethylene, or polypropylene fibers), or a combination of natural and/or synthetic fibers; or coated woven or nonwoven webs. Preferably the belt comprises a nonwoven web of synthetic fibers. The belt may comprise a stretchable nonwoven. More preferably, the belt comprises an inner hydrophobic, non-stretchable nonwoven material and an outer hydrophobic, non-stretchable nonwoven material.

The belt elastic material 96 comprises a waist elastic material 98 and a side elastic material 100. The waist elastic material 98 may comprise one or more of elastic elements such as strands or panels extending in the transverse direction. The side elastic material 100 also may comprise one or more of elastic elements such as strands or panels extending in the transverse direction. The waist elastic material 98 is continuously disposed along the transverse waist border 88 of the front and back belt 84, 86. The side elastic material 100 is preferably disposed in the side panel 82 of the front and back belt 84, 86. In the embodiment shown in FIG. 2, the waist elastic material 98 and the side elastic material 100 comprise a plurality of elastic strands which are disposed at a constant interval in the longitudinal direction. Alternatively, the waist elastic material 98 and the side elastic material 100 may be disposed at a different interval in the longitudinal direction. No elastic material may be provided in a portion of the central panel 80 of the front and back belt 84, 86 which overlaps with the absorbent core 62, preferably with the front and back waist panel 52, 54 of the main body 38. Alternatively, no elastic material may be provided in the entirety of the central panel 80. However, an elastic material may be provided in the central panel 80 if it is necessary. The belt elastic material 96 is interposed between the outer layer 92 and the inner layer 94 and joined therebetween in an uncontracted condition of the belt elastic material 96 such that the front and back belt 84, 86 provides elasticity when the diaper 20 is used.

The outer cover layer 42 is disposed on the outer surface 22 of the diaper 20 and covers the crotch panel 56 of the absorbent main body 38. The outer cover layer 42 has a generally rectangular shape having longitudinal side portions 114 and transverse end portions 116 (refer to FIG. 5). The longitudinal side portion 114 extends transversely outward beyond the longitudinal side edge 48 of the main body 38. The longitudinal side portion 114 is provided with a leg elastic material 118 to form an elastic leg cuff 122 (refer to FIG. 3). The leg elastic material 118 is disposed so as to extend generally longitudinally along the longitudinal side portion 114. The leg elastic material 118 may be disposed at least in the crotch region 30 of the diaper 20 and may not be disposed along the entirety of the longitudinal side portion 114. In order to form the elastic leg cuff 122 in the embodiment, the longitudinal side portion 114 is folded to form a sleeve 120 to encase the leg elastic material 118. The transverse end portion 116A of the longitudinal side portion 114 is folded toward the longitudinal centerline L of the main body 38 and tacked down in the folded configuration by any known means such as adhesives, heat bonding, pressure bonding, ultrasonic bonding, etc. The transverse end portion 116A is preferably folded inwardly so as to be adjacent the liquid impervious backsheet 60 of the main body 38 and is joined onto itself by a bonding means 119 to maintain its folded configuration (refer to FIGS. 4 and 6). The transverse end portion 116A may be also joined to the liquid impervious backsheet 60 by a bonding means 121. The longitudinal side portion 114 in the crotch region 30 is free from attachment (refer to FIGS. 3 and 6) such that the longitudinal side portion 114 serves as the elastic leg cuff 122 when the diaper 20 is used. Alternatively, the transverse end portion 116A may be folded onto the longitudinal side edge 48 of the main body 38. Alternatively, the transverse end portion 116A may be folded outwardly so as to be away from the liquid impervious backsheet 60.

The outer cover layer 42 comprises a material separate from the material of the inner layer 94 and the outer layer 92 constituting the elastic belt 40. The outer cover layer 42 may comprise two of more layer of materials. The outer cover layer 42 may comprise any known materials and may comprise materials as used for the front and back belt 84, 86 as explained above. Preferably the outer cover layer 42 comprises a single layer of nonwoven web of synthetic fibers. More preferably, the outer cover layer 42 comprises a single layer of hydrophobic, non-stretchable nonwoven material.

The outer cover layer 42 covers the crotch panel 56 of the absorbent main body 38. The outer cover layer 42 may extend into and cover the front waist panel 52 and the back waist panel 54 of the main body 38. The outer cover layer 42 is directly joined to and covers the liquid impervious backsheet 42 of the main body 38. In the configuration where the transverse end portion 116A of the longitudinal side portion 114 is folded inwardly so as to be adjacent the liquid impervious backsheet 60 of the main body and joined onto itself by the bonding means 120, the central panel 80 of the front and back belt 84, 86 is joined to the front waist panel 52 and the back waist panel 54 of the main body 38 through the outer cover layer 42. Thus, the outer cover layer 42 is sandwiched between the front and back belt 84, 86 and the liquid impervious backsheet 60 of the main body 38. The transverse end portion 116A is hidden underneath the front and back belt 84, 86. The front belt 84 and the back belt 86 are joined at the seam 32 to form the ring-like elastic belt 40. However, the front waist panel 52 and the back waist panel 54 are not directly joined along the longitudinal side edges 48 but are only indirectly joined through the front and back belt 84, 86.

Figure 6:
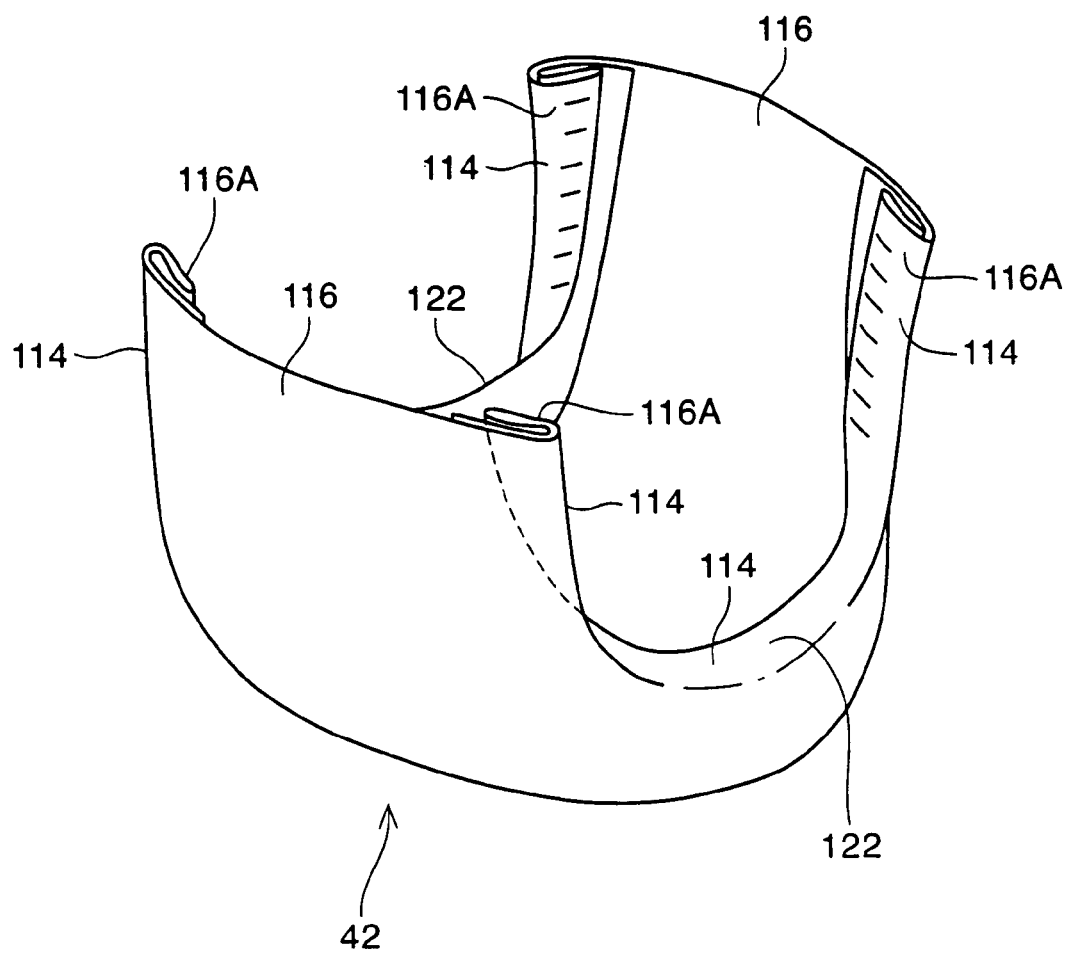
FIG. 6 is a schematic perspective view of the outer cover layer in a typical in-use configuration without showing other elements of the pull-on garment.
Figure 7:
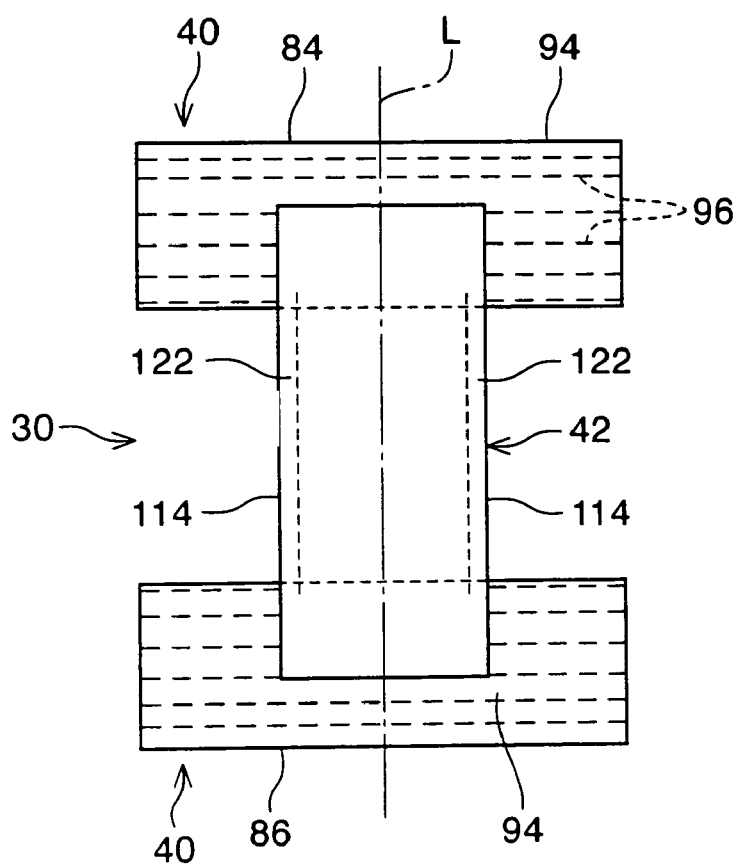
FIG. 7 is a schematic top plan view of the combination of the ring-like elastic belt and the outer cover layer without showing an absorbent man body.
Figure 8:
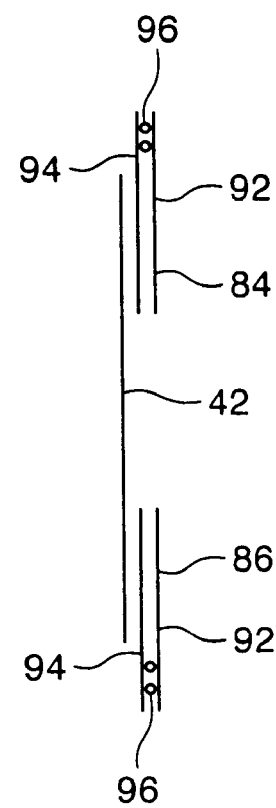
FIG. 8 is a schematic cross-sectional view of FIG. 7 taken along the longitudinal centerline L.
Figure 9:
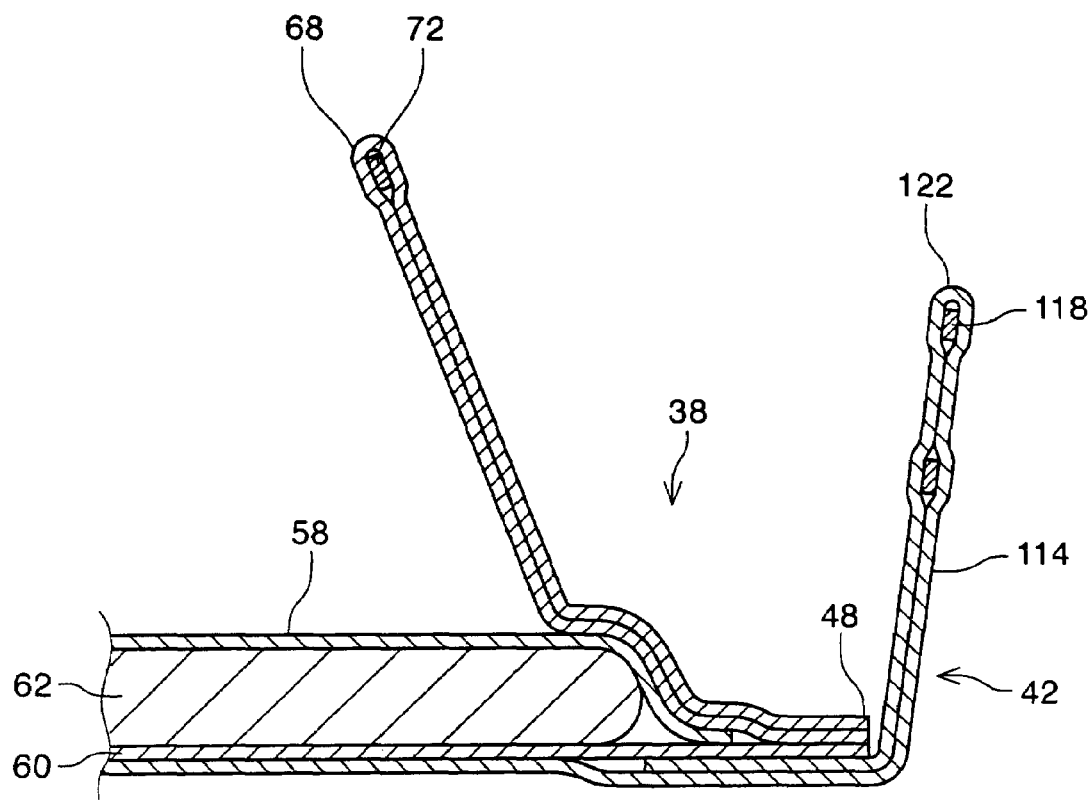
FIG. 9 is a cross-sectional view showing a typical in-use configuration of the portion shown in FIG. 3.

FIG. 7 shows a schematic top plan view of a combination of a ring-like elastic belt and an outer cover layer of the present invention without showing an absorbent main body. FIG. 8 is a schematic cross-sectional view of FIG. 7 taken along the longitudinal centerline L. The front and back belt 84, 86 of the ring-like elastic belt 40 comprises two layers of nonwoven to hold the belt elastic materials 96. However, the ring-like elastic belt 40 formed with two layers of nonwoven (inner layer 94 and outer layer 92) does not extend into the crotch region 30 of the diaper. Instead, the outer cover layer 42 comprising a single layer of nonwoven is disposed in the crotch region 30. This structure is less costly, allows the crotch region 30 of the diaper to be less bulky and eliminates various drawbacks of conventional pull-on diaper. The outer cover layer 42 comprising a nonwoven material also provides a cloth-like appearance together with the ring-like elastic belt 40 comprising a nonwoven material. The outer cover layer 42 is formed with a separate material from the material of the inner layer 94 and the outer layer 92. Therefore, the longitudinal side portion 114 of the outer cover layer 42 can be folded along the longitudinal direction to form the elastic leg cuff 122 or the transverse end portion 116A along the longitudinal side portion 114 can be tacked down as explained above without being interfered by the front and back belt 84, 86. Such folding can be done before the outer cover layer 42 and the front and back belt 84, 86 are joined to one another. The elastic leg cuff 122 formed by the longitudinal side portion 114 extends transversely outward beyond the longitudinal side edge 48 of the main body 38 (not shown in FIGS. 7 and 8). The elastic leg cuff 122 stands up and covers the longitudinal side edge 48 to reduce leakage from the main body 38 when the diaper 20 is used (refer to FIG. 9). Further, the transverse end portion 116A which is inwardly folded and tacked down in its folded configuration ensures the elastic leg cuff 122 to stand up securely in the crotch region 30 (refer to FIG. 6 showing a schematic perspective view of the outer cover layer 42 in a typical in-use configuration without showing other elements of diaper 20).

Figure 10:
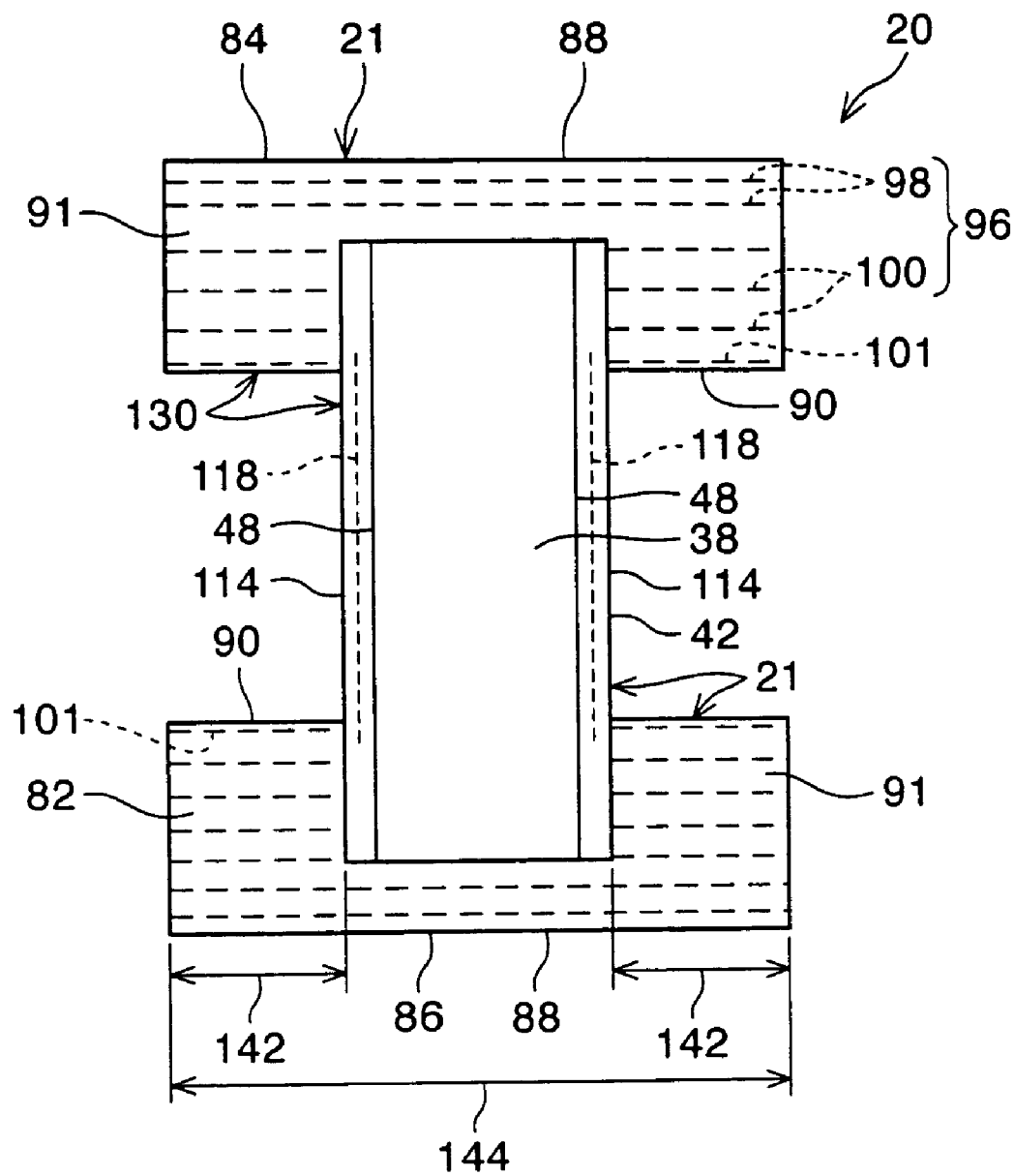
FIG. 10 is a schematic top plan view of the pull-on garment in its flat uncontracted condition showing the inner surface.
Figure 11:
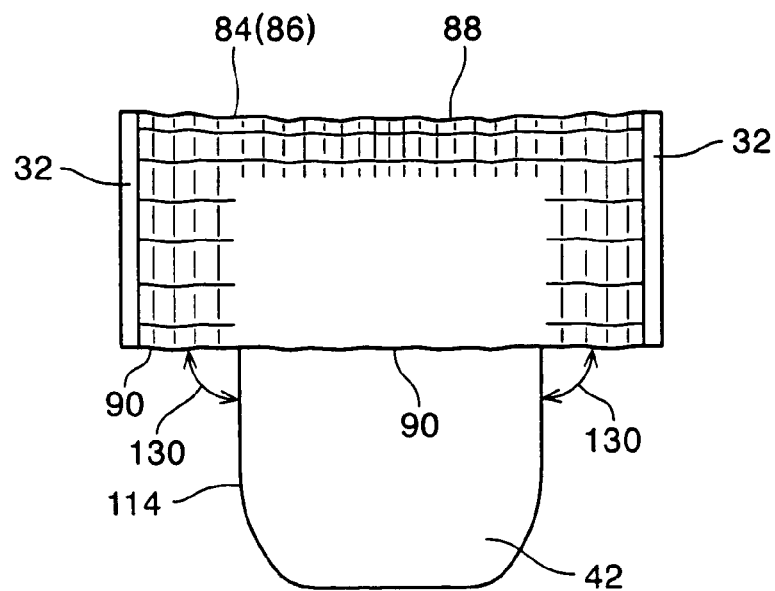
FIG. 11 is a schematic front view of the pull-on garment in its contracted condition for comparison.

FIG. 10 is a schematic top plan view of the pull-on diaper 20 in its flat uncontracted condition showing the inner surface. The pull-on diaper 20 comprises a combination of a transversely extending rectangular front and back belt 84 and 86, a longitudinally extending rectangular main body 38 and a longitudinally extending rectangular outer cover layer 42. In the embodiment shown in FIG. 10, the outer cover layer 42 extends transversely outward beyond the longitudinal side edge 48 of the main body 38. The combination of the outer cover layer 42 and the front and back belt 84, 86 defines the counter edge 21 of the diaper 20. Constructing a pull-on garment with such a combination of generally rectangular shaped members is beneficial to make a costly effective garment which does not require trimming a material of garment. However, the combination of a generally rectangular members such as the front and back belt 84, 86 and the outer cover layer 42 could provide an artificial appearance to the diaper 20 because of the angular shape of the members. Specifically, in the embodiment shown in FIG. 10, the transverse abdomen border 90 of the front and back belt 84, 86 extending transversely straight and the longitudinal side portion 114 of the outer cover layer 42 extending longitudinally straight intersect each other to form a leg opening angle 130 that is a right angle, which decreases a real garment-like appearance and increases an artificial appearance for a garment. Such a garment tends to maintain the angular appearance as shown in FIG. 11 even when the garment is contracted by the belt elastic material 96. The angular appearance of the garment is primarily caused by the transverse abdomen border 90 extending transversely straight and the leg opening angle 130 being a right angle even after the garment is contracted. It is also caused by the angular appearance of the front and back belt 84, 86 having the transverse waist border 88 and the transverse abdomen border 90, both extending transversely straight and the seams extending longitudinally straight even after the garment is contracted.

Figure 12:
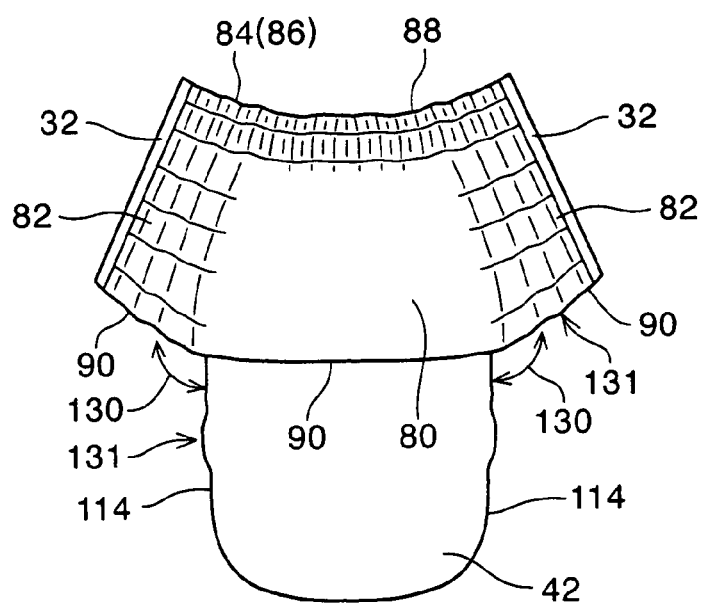
FIG. 12 is a schematic front view of the pull-on garment of FIG. 10 in its contracted condition.

FIG. 12 shows a front view of the pull-on diaper 20 of the present invention in its contracted configuration. The transverse abdomen border 90 of the side panel 82 inclines with respect to the transverse direction such that the leg opening angle 130 formed by the transverse abdomen border 90 and the longitudinal side portion 114 is greater when the diaper 20 is in a contracted configuration as shown FIG. 12 than when the diaper 20 is in an uncontracted configuration as shown in FIG. 10. The leg opening contour 131 formed by the transverse abdomen border 90 and the longitudinal side portion 114 of the outer cover layer 42 in the front view of the contracted diaper 20 is similar to a curved leg opening contour. Therefore, such a configuration contributes to increase a real garment-like appearance of the diaper 20 especially around the leg opening when the user takes a fresh garment out of the package. In addition, the seam 32 is inclined with respect to the longitudinal direction and the transverse waist border 88 is curved when the diaper 20 is contracted. These shape the front and back belt 84, 86 to increase a real garment-like appearance when the diaper 20 is contracted. The leg opening angle 130 may be between 95 degree and 145 degree and preferably between 110 and 130 degree to increase a real garment-like appearance in a contracted condition of the garment. The difference of the leg opening angle 130 between when the diaper is uncontracted and when the diaper is contracted may be between 10 degree and 50 degree and preferably between 20 degree and 40 degree.

Figure 13:
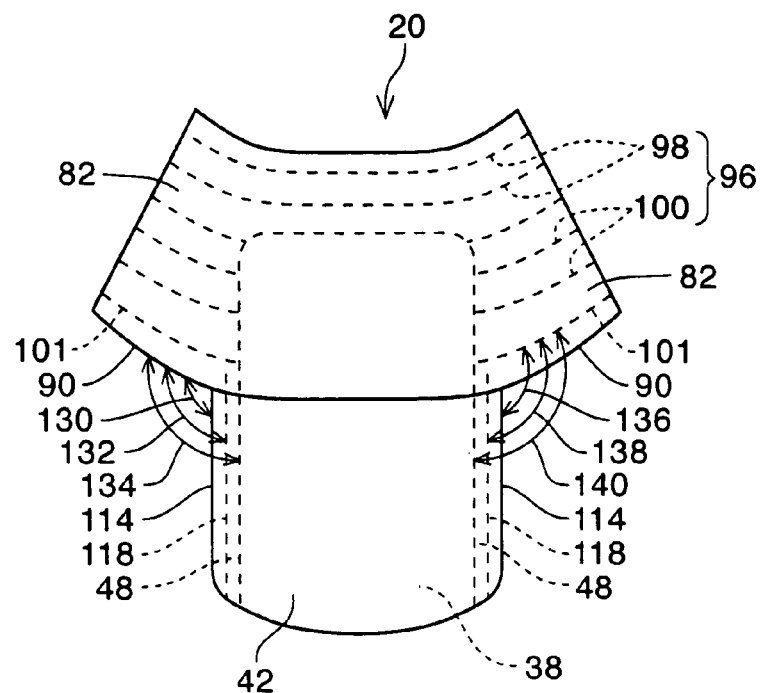
FIG. 13 is a schematic front view of the pull-on garment to explain a positional relationship of various elements of the garment in its contracted condition.

FIG. 13 shows a schematic front view of the pull-on diaper 20 shown in FIG. 12 to explain the positional relationship of various elements of the diaper 20. Because FIG. 12 is only schematically drawn, the number of the belt elastic material in FIG. 10 is different from FIG. 1 or 2. FIG. 13 shows other elements of the diaper 20 such as the absorbent main body 38, the belt elastic material 96 having the waist elastic material 98 and the side elastic material 100, and the leg elastic material 118. The main body 38 extends generally in the longitudinal direction such that the longitudinal side edge 48 of the main body 38 extends generally in the longitudinal direction in an uncontracted configuration (refer to FIG. 10). The bottom side elastic material 101 is disposed generally in parallel to the transverse abdomen border 90 in an uncontracted configuration. The leg elastic material 118 extends generally in parallel to the longitudinal side portion 114 of the outer cover layer 42 and/or the longitudinal side edge 48 of the main body 38 in an uncontracted configuration. As explained above, the transverse abdomen border 90 of the side panel 82 inclines with respect to the transverse direction such that the leg opening angle 130 formed by the transverse abdomen border 90 and the longitudinal side portion 114 is greater when the diaper 20 is in a contracted configuration than when the diaper 20 is in an uncontracted configuration (refer to FIG. 12). The transverse abdomen border 90 also forms the leg opening angle 132 with the leg elastic material 118 and the leg opening angle 134 with the longitudinal side edge 48 of the main body 38. In a contracted configuration of the diaper 20, the leg opening angle(s) 132 and/or 134 are (is) greater when the diaper 20 is in a contracted configuration than when the diaper 20 is in an uncontracted configuration. The bottom side elastic material 101 forms the leg opening angle 136 with the longitudinal side portion 114 of the outer cover layer 42, the leg opening angle 138 with the leg elastic material 138, and the leg opening angle 140 with the longitudinal side edge 48 of the main body 38. In a contracted configuration of the diaper 20, the leg opening angle(s) 136, 138 and/or 140 are (is) greater when the diaper 20 is in a contracted configuration than when the diaper 20 is in an uncontracted configuration.

Figure 14:
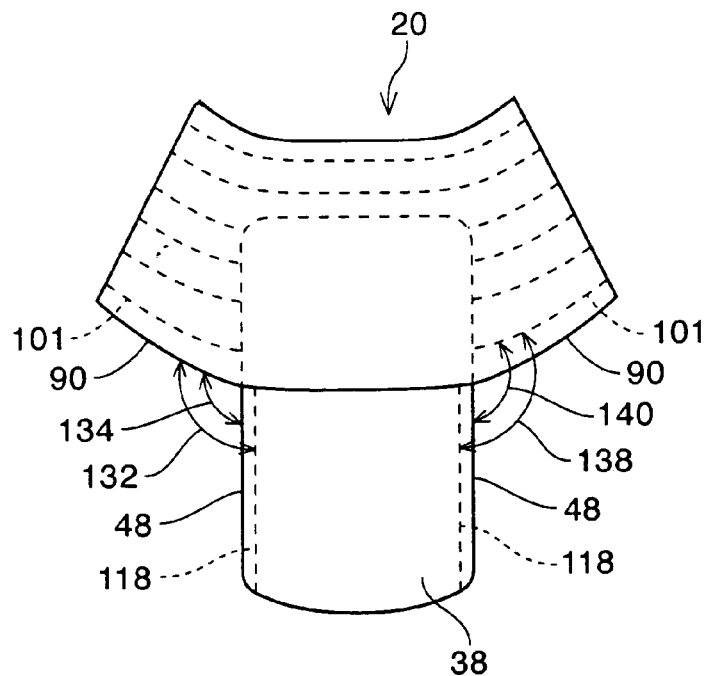
FIG. 14 is a schematic front view of an alternative embodiment of the pull-on garment to explain a positional relationship of various elements of the garment in its contracted condition.

FIG. 14 shows an alternative embodiment of the pull-on diaper 20. The pull-on diaper 20 shown in FIG. 14 does not have an outer cover layer 42. The leg elastic material 118 is directly joined to the absorbent main body 38 along the longitudinal side edge 48. In this embodiment, the transverse abdomen border 90 forms the leg opening angle 132 with the leg elastic material 118 and the leg opening angle 134 with the longitudinal side edge 48 of the main body 38. The bottom side elastic material 101 forms the leg opening angle 138 with the leg elastic material 138 and the leg opening angle 140 with the longitudinal side edge 48 of the main body 38. The leg opening angle 134 may be between 95 degree and 145 degree and preferably between 110 and 130 degree to increase a real garment-like appearance in a contracted condition of the garment. The difference of the leg opening angle 134 between when the diaper is uncontracted and when the diaper is contracted may be between 10 degree and 50 degree and preferably between 20 degree and 40 degree.

Figure 15:
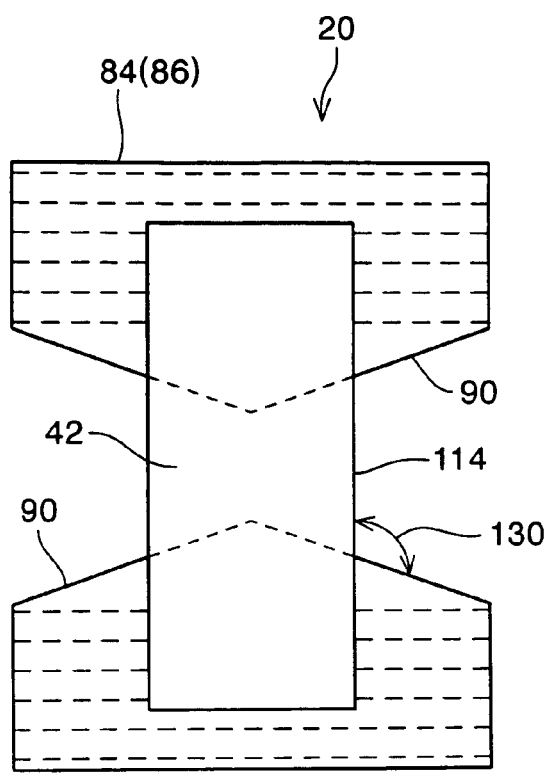
FIG. 15 is a schematic top plan view of an alternative embodiment of the pull-on garment in its flat uncontracted condition showing the inner surface.
Figure 16:
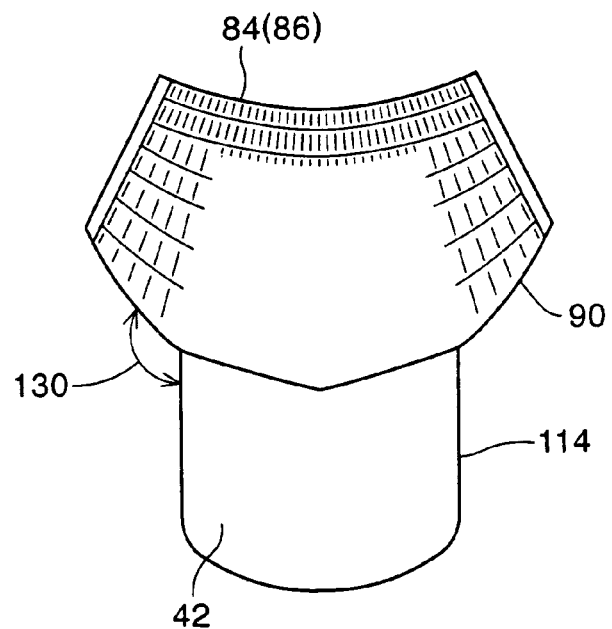
FIG. 16 is a schematic front view of the pull-on garment of FIG. 15 in its contracted condition.

FIGS. 15 and 16 shows another alternative embodiment of the pull-on diaper 20. The front and back belt 84, 86 is shaped in the embodiment shown in FIGS. 15 and 16. More concretely, the transverse abdomen border 90 of the front and back belt 84, 86 has a convex shape which protrudes towards the other side of the front and back belt 84, 86. Therefore, the leg opening angle 130 formed by the transverse abdomen border 90 and the longitudinal side portion 114 of the outer cover layer 42 is greater than 90 degree in an uncontracted configuration of the diaper 20. The leg opening angle 130 is greater when the diaper 20 is contracted than when the diaper 20 is uncontracted. It also contributes to increase a real garment-like appearance. Alternatively, the front and back belt 84, 86 may be shaped such that the leg opening angle 130 is less than 90 degree in an uncontracted configuration of the diaper 20 but is greater than 90 degree in a contracted configuration of the diaper 20. The front and back belt 84, 86 may also have a different shape from one another.

The belt elastic material 96 is provided with the belt layer 91 of the front and back belt 84, 86 such that the leg opening angle is greater when the diaper 20 is in a contracted configuration than when the diaper 20 is in an uncontracted configuration. More concretely, when the waist elastic material 98 and the side elastic material 100 are joined to the belt layer 91, the waist elastic material 98 and the side elastic material 100 are stretched to different stretched lengths. The waist elastic material 98 is stretched greater than the side elastic material 100 when they are joined to the belt layer 91. When the diaper 20 having the front and back belt 84, 86 thus formed is contracted by the returning force of the waist elastic material 98 and the side elastic material 100, the transverse width of the transverse waist border 88 is shorter than the transverse width of the transverse abdomen border 90 to shape the front and back belt 84, 86 as shown in FIG. 12.

The waist elastic material 98 may be stretched to between 100% and 300%, preferably between 150% and 250% when being joined to the belt layer 91 to obtain a garment having an aesthetic appearance. The side elastic material 100 may be stretched to between 50% and 250%, preferably between 100% and 200% for the same purpose. Herein, the stretchability of, e.g., "100%" means that a material is stretched to twice as long as the unstretched material length. When the waist elastic material 98 comprises a plurality of elastic materials, the stretched lengths of each elastic materials may be different. Likewise, when the waist side elastic material 100 comprises a plurality of elastic materials, the stretched lengths of each elastic materials may be different. It is preferable that the elastic material disposed adjacent to the transverse waist border 88 is stretched greater than the elastic material disposed adjacent to the transverse abdomen border 90. While the side elastic material 100 may extend to cross the absorbent main body 38 and the side elastic material 100 on the left side panel and the right side panel may be connected, it is preferable that the side elastic material 100 is not disposed on the absorbent main body 38 so that the portion of the diaper 20 where the absorbent core is present is not contracted. It also helps shaping the front and back belt 84, 86 as shown in FIG. 12 by not contracting the portion of the central panel 80. The transverse width 142 of the belt layer 91 in which the side elastic material 100 is joined (i.e., the transverse width of the side panel 82) is between 50% and 80% of the transverse width 144 of the belt layer 91 in which the waist elastic material 98 is joined (i.e., the transverse width of the transverse waist border 88) in an uncontracted configuration of the disposable pall-on diaper 20.

Figure 17:
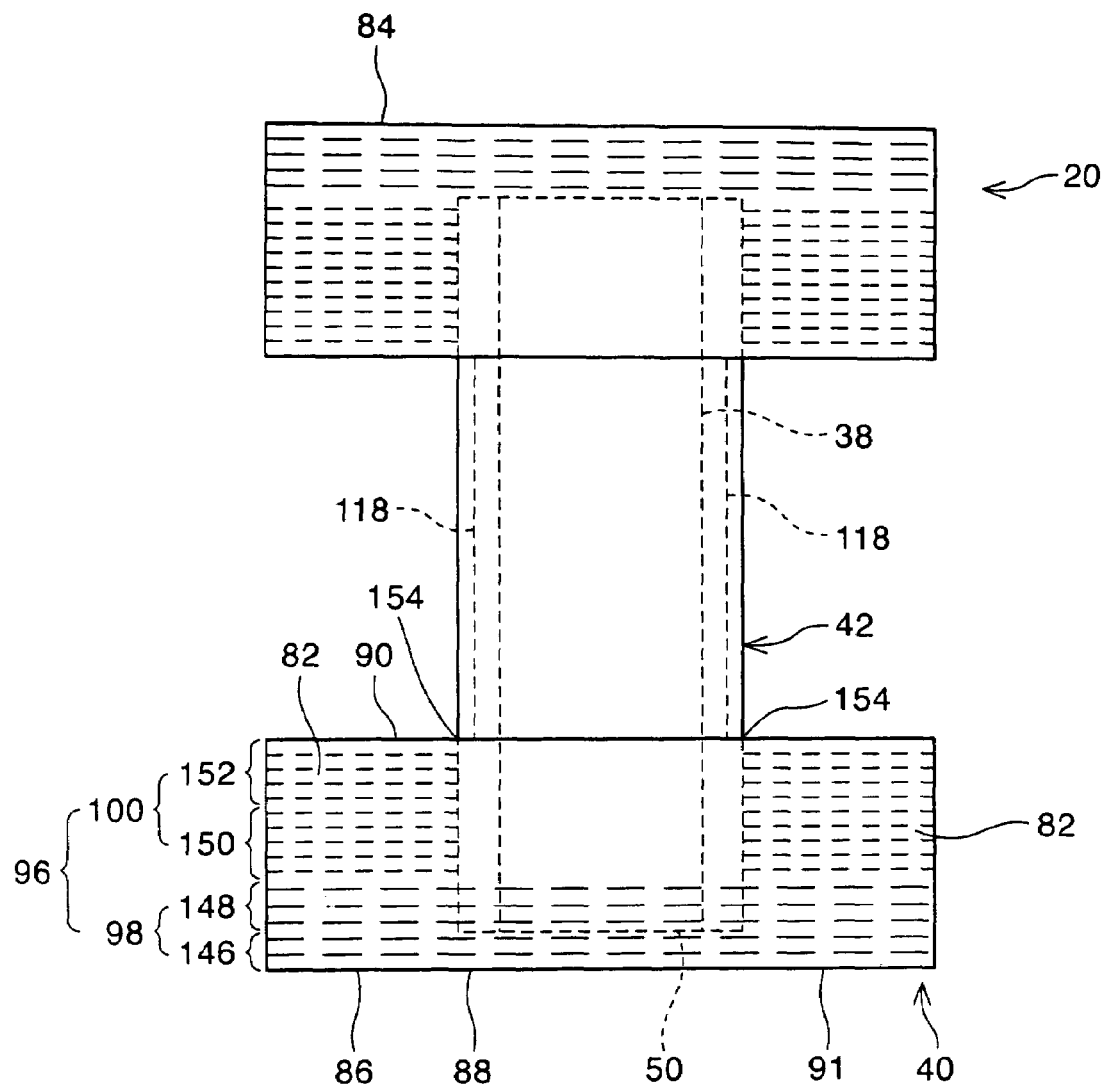
FIG. 17 is a schematic top plan view of the pull-on garment in its flat uncontracted condition showing the outer surface.

FIG. 17 shows a schematic top plan view of the pull-on diaper 20 in its flat uncontracted condition showing the outer surface. As explained above, the belt elastic material 96 comprises the waist elastic material 98 and the side elastic material 100. The waist elastic material 98 disposed in the back belt 86 further comprises a waist border elastic material 146 and a waist anchoring elastic material 148, each of which may comprise a plurality of elastic elements such as strands or panels. The waist border elastic material 146 is disposed along the transverse waist border 88 of the back belt 86. The waist anchoring waist elastic material 148 is disposed extending transversely between the waist border elastic material 146 and the side elastic material 100. The side elastic material 100 disposed in the back belt 86 further comprises a side panel elastic material 150 and a side leg elastic material 152. The side panel elastic material 150 is disposed in the middle of the side panel 82 of the back belt 86. The side leg elastic material 152 is disposed along the transverse abdomen border 90 of the back belt 86. The waist elastic material 98 and the side elastic material 100 disposed in the front belt 84 may have the same structure as those disposed in the back belt 86.

The waist anchoring elastic material 148 generates a greater stress against an applied extension force than the side elastic material 100 in the back belt 86. The applied extension force is applied to an elastic material of the garment to stretch the elastic material for fitting the garment to the wearer. The waist anchoring elastic material 148 preferably generates a greater stress against an applied extension force than the waist border elastic material 146 in the back belt 86. The waist anchoring elastic material 148 also preferably generates a greater stress against an applied extension force than the side leg elastic material 152 in the back belt 86. Further the waist anchoring elastic material 148 preferably generates a greater stress against an applied extension force than the side panel elastic material 150 in the back belt 86. The stress generated by the waist border elastic material 146, the side leg elastic material 152 and the side panel elastic material 150 may be the same or may be different from each other. The waist anchoring elastic material 148 generates a stress at 150% stretch of between 2 N and 6 N, preferably between 3 N and 5 N. The waist border elastic material 146 generates a stress at 150% stretch of between 0.2 N and 2.2 N, preferably between 0.4 N and 2 N. The side elastic material 100 generates a stress at 150% stretch of between 1 N and 5 N, preferably between 2 N and 4 N. The stress of the side elastic material 100 equals to the total stress adding the stress of the side leg elastic material 152 and the stress of the side panel elastic material 150. The stress of each elastic material 146, 148 and 100 is determined by measuring the stress of each elastic element constituting the elastic material 146, 148 and 100 and adding each stress of the elastic elements. A tensile tester suitable for use herein is available from Instron Corporation (100 Royall Street, Canton, Mass. 02021, U.S.A.) as Code No. Instron 5564. The gauge Length should be 20 mm and the crosshead speed should be 500 mm/min. Desired stress can be achieved by any known means such as changing the material elastic and changing the thickness of the elastic material.

Figure 18:
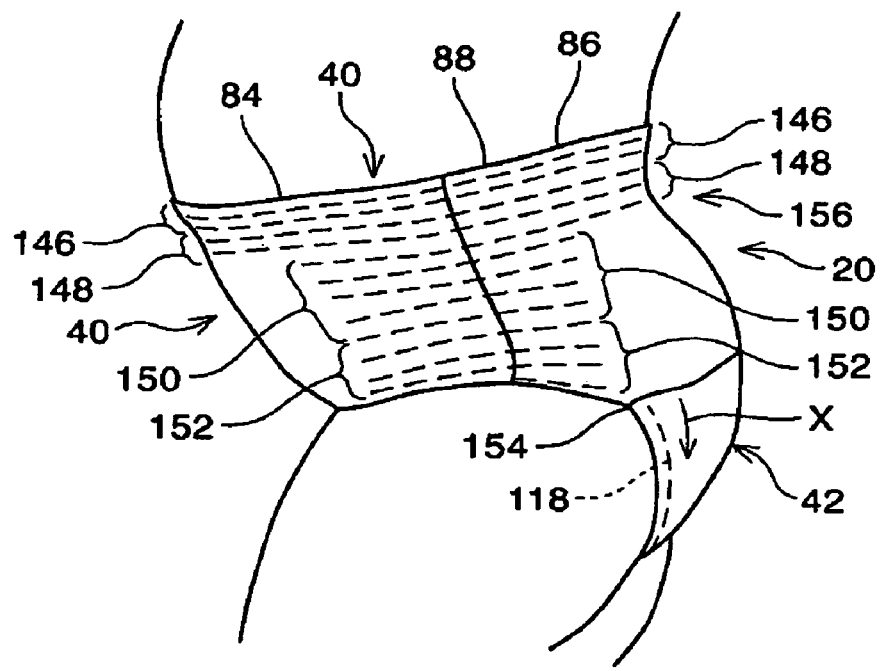
FIG. 18 is a schematic side view of the pull-on garment in its use condition.
Figure 19:
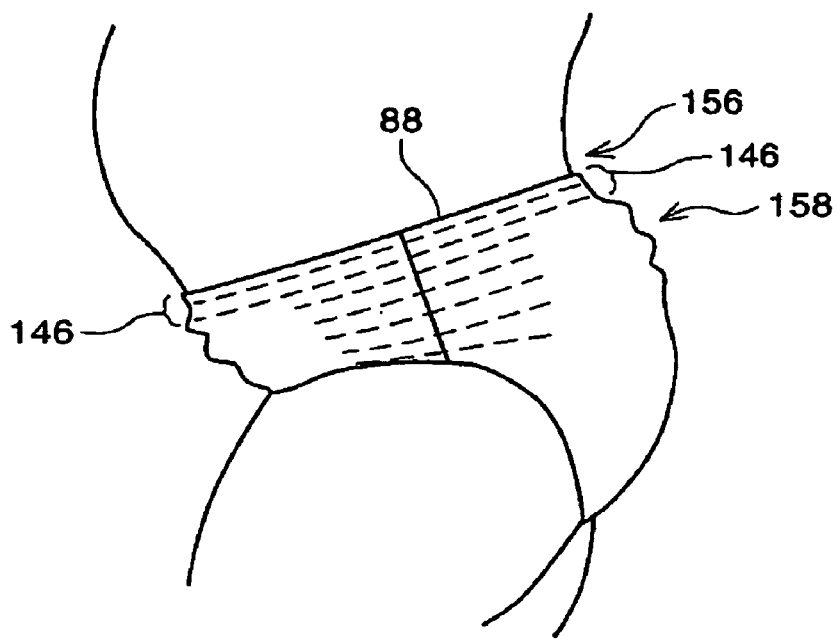
FIG. 19 is a schematic side view of a conventional pull-on garment in its use condition.

The diaper 20 having the waist anchoring elastic material 148 generating a greater stress against an applied extension force than the side elastic material 100 in the back belt 86 improves a detachment problem between the ring-like elastic belt 40 and the outer cover layer 42 covering the absorbent main body 38 and improves an aesthetic appearance of the diaper 20 when it is worn on the wearer. The waist anchoring elastic material 148 is fitted to the concave back waist 156 above the hip of the wearer as shown in FIG. 18 and generates the stress greater than the side elastic material 100 to anchor the diaper 20 on the wearer. The leg side elastic material 152 of the side elastic material 100, however, generates the stress less than the waist anchoring elastic material 148 and readily stretches to follow the downward force X generated by the leg elastic material 118 and the absorbent main body 38 (not shown in FIG. 18) heavily loaded by urine or other body exudates. Therefore, the detachment problem can be improved around the juncture 154 between the outer cover layer 42 covering the absorbent main body 38 and the elastic belt 40 joined with the side leg elastic material 152. The waist anchoring elastic material 148 also generates a greater stress against an applied extension force than the waist border elastic material 146 such that the waist anchoring elastic material 148 generates an force anchoring the diaper 20 to the concave back waist 156 of the wearer. Since the waist border elastic material 146 only generates a less stress than the waist anchoring elastic material 148, the waist border elastic material 146 readily stretches to follow the movement of the wearer to surround the wearer's high back waist above the concave back waist 156. It improves an aesthetic appearance of the diaper 20 when it is worn on the wearer. The front panel 84 may have the same structure such that the waist anchoring elastic material may generate a greater stress against an applied extension force than the waist border elastic material, the side leg elastic material, and/or the side panel elastic material. In contrast, FIG. 19 shows a conventional garment having a waist elastic material generating a high stress to anchor the garment on the wearer's body. Since the waist elastic material generates a high stress, the transverse waist border 88 sags down to conform to the shape of the wearer's concave back waist 156. It causes a bunching 158 of the garment 20.

The waist border elastic material 146, the waist anchoring elastic material 148 and the side elastic material 100 are stretched when they are joined to the belt layer 91 of the back belt 86. It is preferable that the waist anchoring elastic material 148 is stretched less than the waist border elastic material 146 and the side elastic material 100 when being joined to the belt layer 91. While the waist anchoring elastic material 148 generates a high stress for anchoring, the waist anchoring elastic material 148 being less stretched when being joined to the belt layer 91 suppresses giving an excessive force to the wearer's skin to avoid skin disorders. The waist border elastic material 146 is preferably stretched greater than the side elastic material 100 when they are joined to the belt layer 91. This increases a real garment-like appearance in a contracted condition of the diaper 20 as explained above.

The waist anchoring elastic material 148 may be disposed to overlap with a portion of the absorbent main body 38. In the embodiment shown in FIG. 17, the waist anchoring elastic material 148 overlaps with the main body 38 adjacent the transverse end edge 50. This allows to suppress giving an excessive force to the wearer's skin to avoid skin disorders.

The outer layer 92 of the belt layer 91 is folded along the transverse waist border 88 toward the liquid pervious topsheet 58 of the absorbent main body 38 to form an end flap 112 as explained above. The end flap 112 covers a portion of the absorbent main body 38 at the back region 28 as shown in FIG. 2. The end flap 112 also overlaps with the waist anchoring elastic material 148. Alternatively, the inner layer 94 of the belt layer 91 may be folded along the transverse waist border 88 to form an end flap 112. Since the end flap 112 intervenes between the waist anchoring elastic material 148 and the wearer's skin when the diaper 20 is worn by the wearer, the end flap 112 functions to suppress giving an excessive force to the wearer's skin to avoid skin disorders.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable pull-on garment comprising:
    an absorbent main body comprising a liquid pervious topsheet, a liquid impervious backsheet and an absorbent core disposed therebetween, and having longitudinal side edges, transverse end edges, a front waist panel, a back waist panel and a crotch panel between the front waist panel and the back waist panel; and
    a ring-like elastic belt joined to the backsheet in the front waist panel and the back waist panel of the absorbent main body to form one waist opening and two leg openings, the ring-like elastic belt not extending into the crotch panel of the absorbent main body,
    wherein the ring-like elastic belt comprises a front belt and a back belt each having laterally opposing side panels, a central panel between the side panels, a transverse waist border, and a longitudinally opposing transverse abdomen border, the waist border being disposed longitudinally beyond the respective end edge of the absorbent main body, each of the front belt and the back belt comprises a belt layer and a belt elastic material joined to the belt layer, the belt elastic material comprising a transverse waist elastic material disposed adjacent to the waist border and a transverse side elastic material disposed only in each of the side panels adjacent to the abdomen border laterally outboard of the respective waist panel of the absorbent main body and not overlapping the respective waist panel, the respective waist panel not being overlapped by any transverse elastic material between the side elastic material disposed in the side panels, the waist elastic material of the back belt comprising a transverse waist border elastic material disposed between the waist border of the back belt and the transverse end edge of the absorbent main body adjacent to the back belt, and the belt elastic material is provided with the belt layer such that a leg opening angle formed by the transverse abdomen border and each of the longitudinal side edges of the absorbent main body is greater when the disposable pull-on garment is in a contracted configuration than when the disposable pull-on garment is in an uncontracted configuration.

2. The disposable pull-on garment of claim 1 wherein the pull-on garment comprises an outer cover layer, the outer cover layer comprises a material separate from the ring-like elastic belt, the outer cover layer has longitudinal side portions and transverse end portions, the outer cover layer covers the crotch panel of the absorbent main body, and each of the longitudinal side portions of the outer cover layer is provided with a leg elastic material to form an elastic leg cuff.

3. The disposable pull-on garment of claim 2 wherein each of the longitudinal side portions of the outer cover extends transversely beyond the respective longitudinal side edge of the absorbent main body.

4. The disposable pull-on garment of claim 3 wherein the belt elastic material is provided with the belt layer such that a leg opening angle formed by the transverse abdomen border and each of the longitudinal side portions of the outer cover layer is greater when the disposable pull-on garment is in the contracted configuration than when the disposable pull-on garment is in the uncontracted configuration.

5. The disposable pull-on garment of claim 2 wherein the belt elastic material is provided with the belt layer such that a leg opening angle formed by the side elastic material and the respective leg elastic material is greater when the disposable pull-on garment is in the contracted configuration than when the disposable pull-on garment is in the uncontracted configuration.

6. The disposable pull-on garment of claim 5 wherein the side elastic material is disposed to extend generally in the transverse direction and the leg elastic material is disposed to extend generally in the longitudinal direction when the disposable pull-on garment is in the uncontracted configuration.

7. The disposable pull-on garment of claim 1 wherein the waist elastic material and the side elastic material are stretched when being joined to the belt layer, the waist elastic material being stretched greater than the side elastic material.

8. The disposable pull-on garment of claim 7 wherein the waist elastic material is stretched to between 100% and 300% and the side elastic material is stretched to between 50% and 250%.

9. The disposable pull-on garment of claim 8 wherein the transverse width of the belt layer in which the side elastic material is joined is between 50% and 80% of the transverse width of the belt layer in which the waist elastic material is joined in the uncontracted configuration.

* * * * *

UNITED STATES PATENT AND TRADEMARK OFFICE
CERTIFICATE OF CORRECTION

PATENT NO. : 7,569,039 B2
APPLICATION NO. : 10/985402
DATED : August 4, 2009
INVENTOR(S) : Toshiyuki Matsuda et al.

It is certified that error appears in the above-identified patent and that said Letters Patent is hereby corrected as shown below:

Column 10

Line 21, delete "waist".

Line 41, delete "pall-on" and insert -- pull-on --.

Signed and Sealed this

Twenty-fifth Day of May, 2010

David J. Kappos
*Director of the United States Patent and Trademark Office*